(12) United States Patent
Readdie et al.

(10) Patent No.: US 9,955,912 B2
(45) Date of Patent: May 1, 2018

(54) MAGNET-BASED MONITORING SYSTEM

(71) Applicants: Mark A. Readdie, Santa Cruz, CA (US); Jeremy G. Chatwin, Santa Cruz, CA (US); Omondi L. Nyong'o, San Francisco, CA (US)

(72) Inventors: Mark A. Readdie, Santa Cruz, CA (US); Jeremy G. Chatwin, Santa Cruz, CA (US); Omondi L. Nyong'o, San Francisco, CA (US)

(73) Assignee: Getchell Technologies LLC, Santa Cruz, CA (US)

( * ) Notice: Subject to any disclaimer, the term of this patent is extended or adjusted under 35 U.S.C. 154(b) by 0 days. days.

(21) Appl. No.: 15/207,879

(22) Filed: Jul. 12, 2016

(65) Prior Publication Data
US 2017/0014071 A1    Jan. 19, 2017

Related U.S. Application Data

(60) Provisional application No. 62/192,062, filed on Jul. 14, 2015.

(51) Int. Cl.
*G08B 23/00* (2006.01)
*A61B 5/00* (2006.01)
*A61F 9/04* (2006.01)

(52) U.S. Cl.
CPC ......... *A61B 5/4833* (2013.01); *A61B 5/6803* (2013.01); *A61F 9/04* (2013.01); *A61B 5/6821* (2013.01); *A61B 2562/0223* (2013.01)

(58) Field of Classification Search
CPC ........ A61B 5/746; A61B 5/0022; A61B 5/024

USPC .................................. 340/561, 573.1–573.4
See application file for complete search history.

(56) References Cited

U.S. PATENT DOCUMENTS

| 5,122,744 | A   |   | 6/1992 | Koch |
|---|---|---|---|---|
| 5,879,292 | A | * | 3/1999 | Sternberg .............. A61F 13/124 600/300 |
| 6,385,482 | B1 |   | 5/2002 | Boksberger et al. |
| 7,561,051 | B1 | * | 7/2009 | Kynor ..................... A61B 5/06 340/572.4 |

(Continued)

FOREIGN PATENT DOCUMENTS

| WO | 1998040757 A1 | 9/1998 |
|---|---|---|
| WO | 2013050735 A1 | 4/2013 |

OTHER PUBLICATIONS

A.R. Fielder et al., "Compliance in amblyopia therapy: objective monitoring of occlusion", British Journal of Ophthalmology, 1995; vol. 79, pp. 585-589.

(Continued)

*Primary Examiner* — George Bugg
*Assistant Examiner* — Sharmin Akhter
(74) *Attorney, Agent, or Firm* — HIPLegal LLP; Judith Szepesi

(57) ABSTRACT

A magnetometer-based monitoring system comprising a magnet integrated with an object whose disposition is to be monitored, a first magnetometer secured in proximity to the object, and a second magnetometer secured at a fixed distance from the first magnetometer in proximity to the object. The monitoring system further comprising a processor to receive data from the first magnetometer and the second magnetometer, and calculate a measurement vector to determine the disposition of the object.

19 Claims, 9 Drawing Sheets

(56) References Cited

U.S. PATENT DOCUMENTS

| | | | |
|---|---|---|---|
| 7,575,550 B1* | 8/2009 | Govari | A61B 5/06 600/424 |
| 8,222,889 B2 | 7/2012 | Oberhoffner | |
| 8,729,892 B2 | 5/2014 | Friedrich | |
| 9,141,194 B1 | 9/2015 | Keyes et al. | |
| 9,262,033 B2 | 2/2016 | Idzik et al. | |
| 9,298,281 B2 | 3/2016 | Fullerton et al. | |
| 2008/0177170 A1 | 7/2008 | Roberts et al. | |
| 2010/0322859 A1* | 12/2010 | Jones | A61B 5/0002 424/9.1 |
| 2012/0041297 A1 | 2/2012 | McGary | |
| 2013/0120157 A1* | 5/2013 | Geva | A61B 5/6832 340/870.16 |

OTHER PUBLICATIONS

Bot Thoughts, "Magnetometer Soft- and Hard-Iron Calibration", <http://diydrones.com/forum/topics/magnetometer-soft-and-hard-iron-calibration>, DIY Drones, Retrieved on Sep. 30, 2016, 19 pages.

H.J. Simonsz et al., "Electronic monitoring of treatment compliance in patching for amblyopia.", Strabismus, Jun. 1999; vol. 7, No. 2, pp. 113-123, Informa Healthcare, London.

Matselenak, Yury, "Advanced hard and soft iron magnetometer calibration for dummies", <http://diydrones.com/profiles/blogs/advanced-hard-and-soft-iron-magnetometer-calibration-for-dummies>, DIY Drones, Retrieved on Sep. 30, 2016, 15 pages.

EP 16179579.4 Extended European Search Report, dated Dec. 12, 2016, 9 pages.

Kai Januschowski et al, "Measuring wearing times of glasses and ocular patches using a thermosensor device from orthodontics", Acta Ophthalmologica: The Ophthalmological Journal of the Nordic Countries, vol. 91, No. 8, Dec. 1, 2013, pp. e635-e640, XP055246470, Denmark.

Pepka, G, "Position and Level Sensing Using Hall-Effect Sensing Technology", Allegro Microsystems, LLC, Version AN295044, Rev. 1, Not dated but Copyright 2006-2013 claimed., <http://www.allegromicro.com/en/Design-Center/Technical-Documents/Hall-Effect-Sensor-IC-Publications/Position-and-Level-Sensing-U>, Retrieved on Sep. 11, 2017, 7 pages.

Various authors, "Magnetometer", Wikipedia, <https://en.wikipedia.org/wiki/Magnetometer#Faraday_Force_Magnetometry>, Retrieved on Sep. 11, 2017, 21 pages.

Yaroslava Chopovska et al: "Electronic recording of occlusion treatment for amblyopia: potential of the new technology", Graefe's Archive for Clinical and Experimental Opthalmology: Incorporating German Journal of Opthalmology, Springer, Berlin, DE, vol. 243, No. 6, Jun. 1, 2005, pp. 539-544.

* cited by examiner

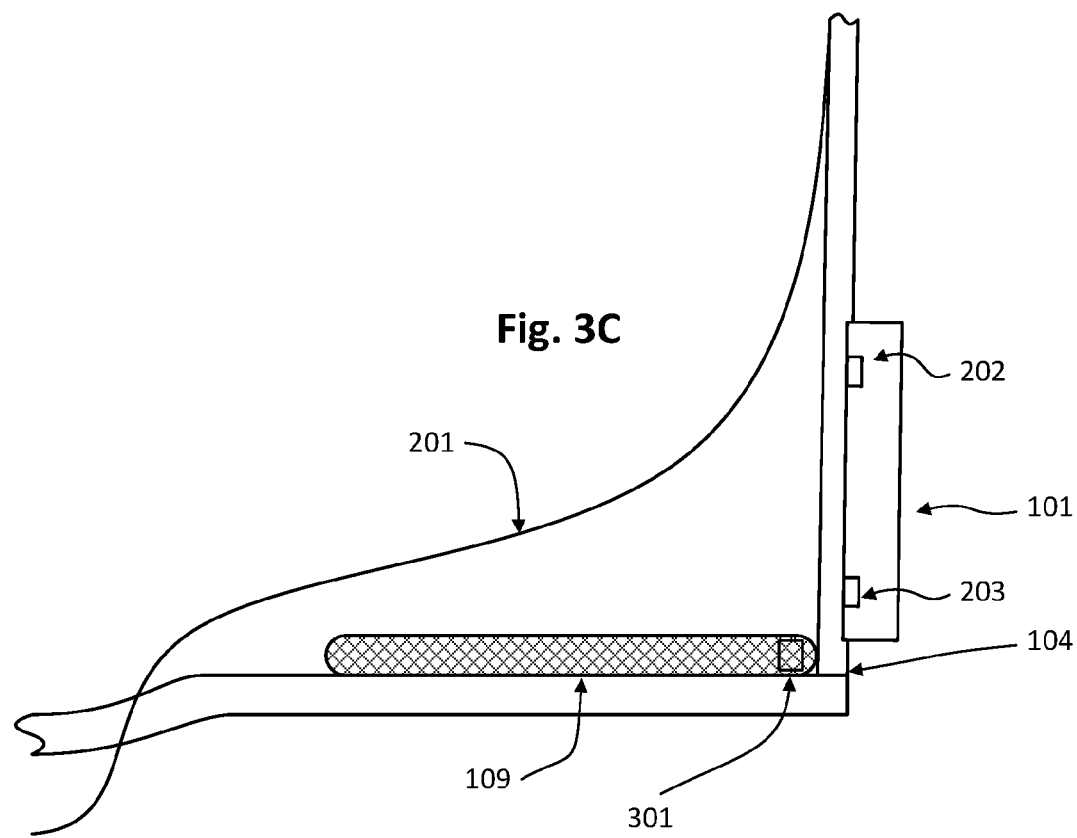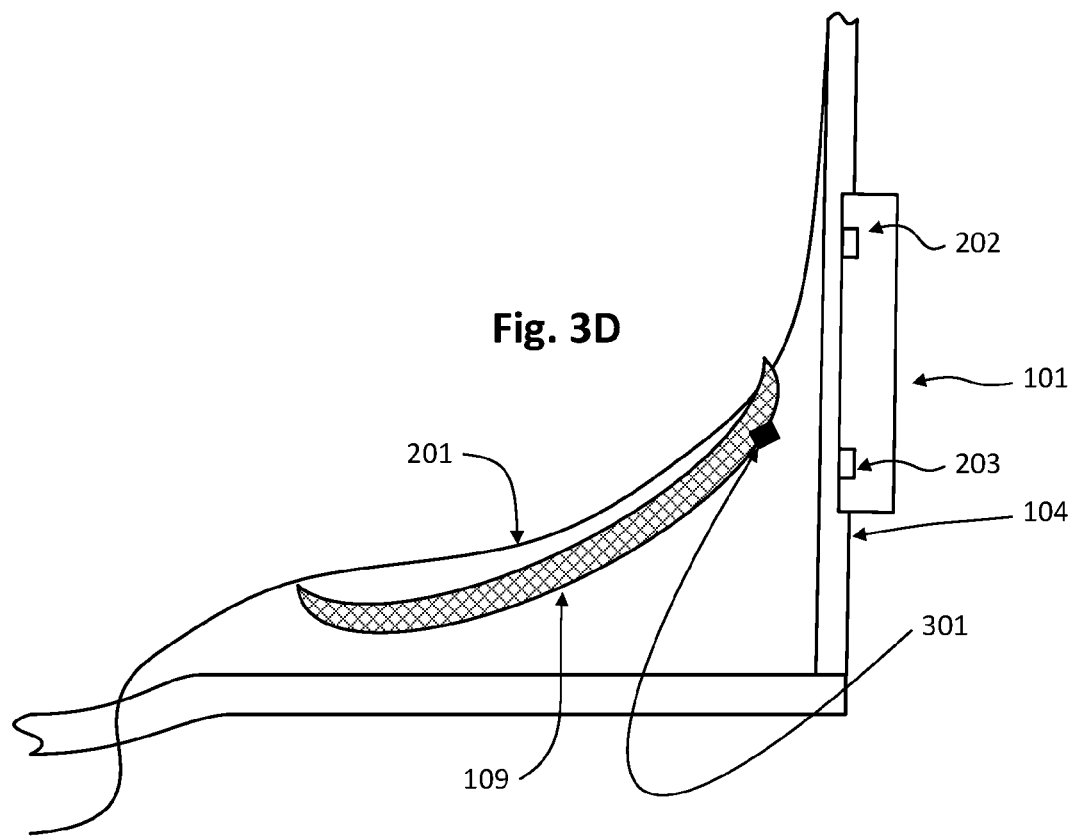

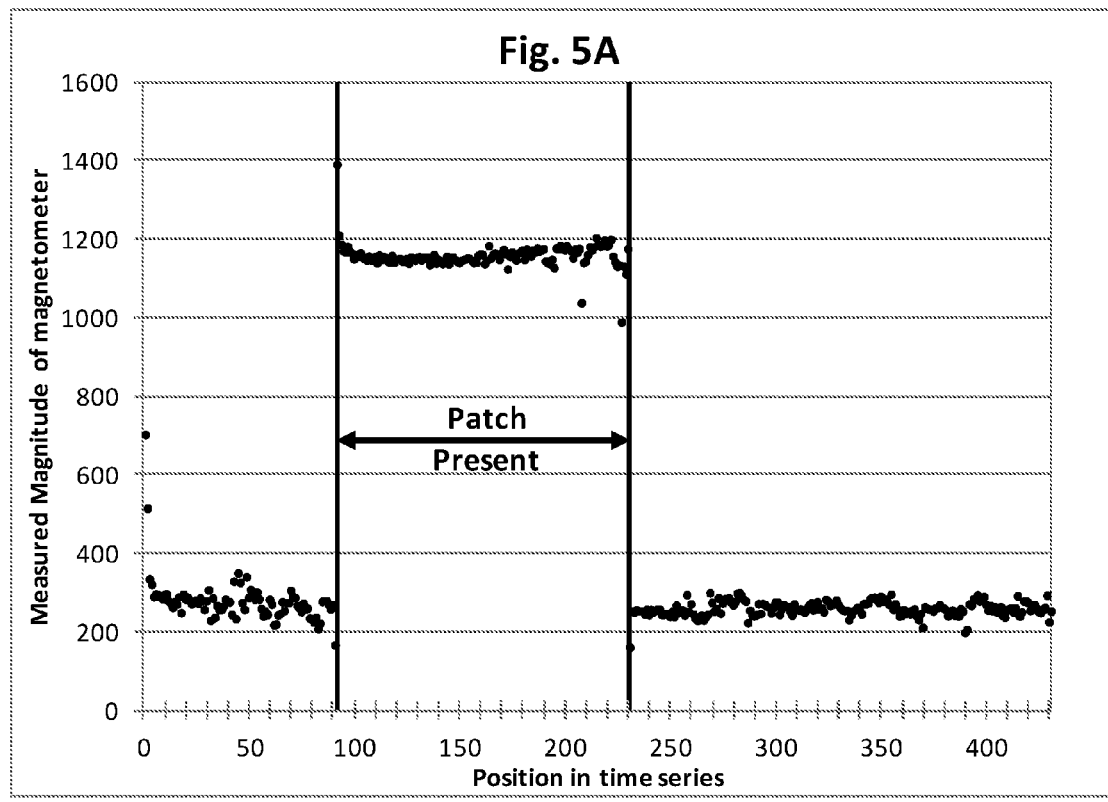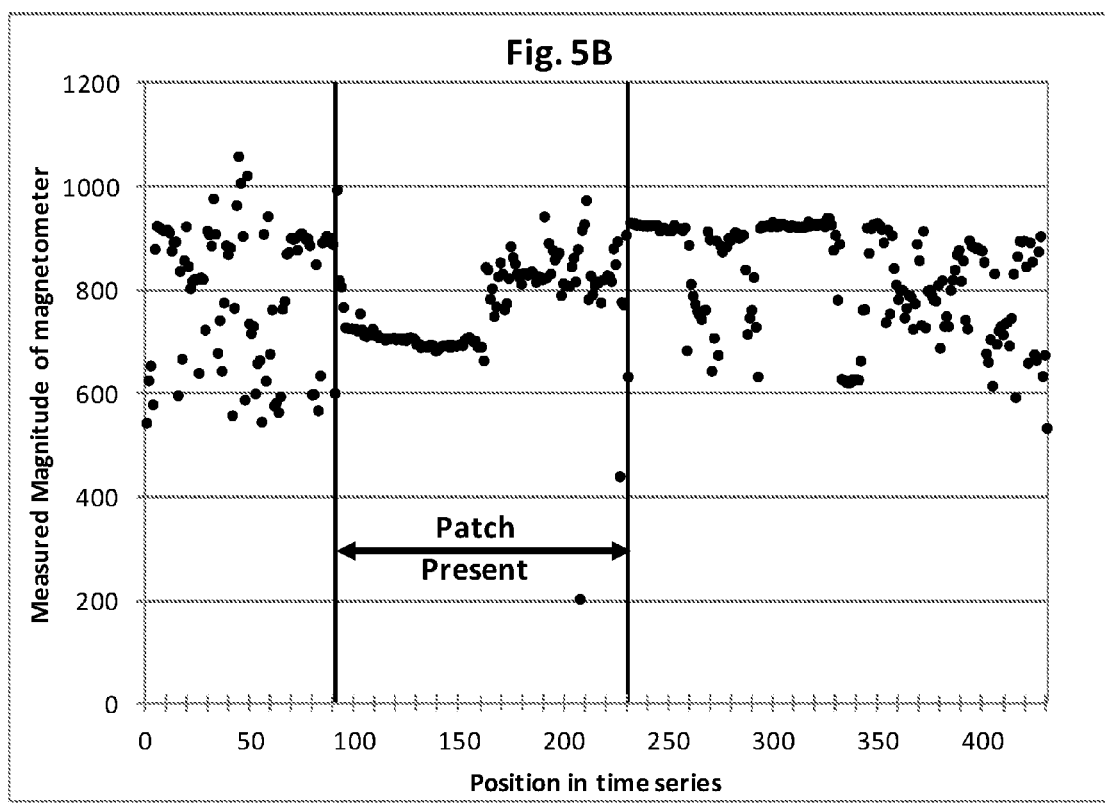

MAGNET-BASED MONITORING SYSTEM

RELATED APPLICATION

The present invention claims priority to U.S. Provisional Application No. 62/192,062, filed on Jul. 14, 2016, and incorporates that application in its entirety.

FIELD

The present invention relates to using magnetometers, and more precisely to the determination of the disposition of an object using magnetometers.

BACKGROUND

Amblyopia is a vision disorder whereby information from one eye is not completely transmitted or not fully processed by the brain in favor of information from the other, "strong" eye. A common treatment modality for Amblyopia is the periodic occlusion of the "strong" eye for a prescribed duration over a specified time period. Occlusion may be achieved with an opaque "patch" that covers the eye by attachment to the face or by attachment to eyeglass lens or frame. This method of periodic occlusion is commonly referred to as "patching." Patching is also used as a treatment of strabismus and other vision disorders.

The most common method of tracking such treatment is asking the patient or caregiver to keep diaries or logs of patching without the use of any automation. The diary is reviewed when the patient next meets with their practitioner. This method relies on the patient or caregiver accurately recording these times. However, this may often be inaccurate.

A prior art apparatus uses two skin contact electrodes added to an adhesive patch and connected to electronics carried in a separate bag. The device seeks to use electrical resistance measurements between the electrodes as a sign of the patch being worn.

Another prior art apparatus attaches a small, self-contained device to a patch and monitors the temperature difference between the front and back of the device, as a signal for the wearing of the patch. This method does not rely on the patient or caregiver remembering to record timings but does require them to remember to transfer the sensor/microcontroller combination from patch to patch.

BRIEF DESCRIPTION OF THE FIGURES

The present invention is illustrated by way of example, and not by way of limitation, in the figures of the accompanying drawings and in which like reference numerals refer to similar elements and in which:

FIGS. 3A, 3C, and 3D illustrate embodiments of a top view of the user's face, showing glasses, patch, and logging device.

FIG. 5A illustrates an exemplary time-series output from an ODM with a single magnetometer, and a large magnet.

FIG. 5B illustrates an exemplary time-series output from an ODM with a single magnetometer, and a small magnet

DETAILED DESCRIPTION

Figure 1:
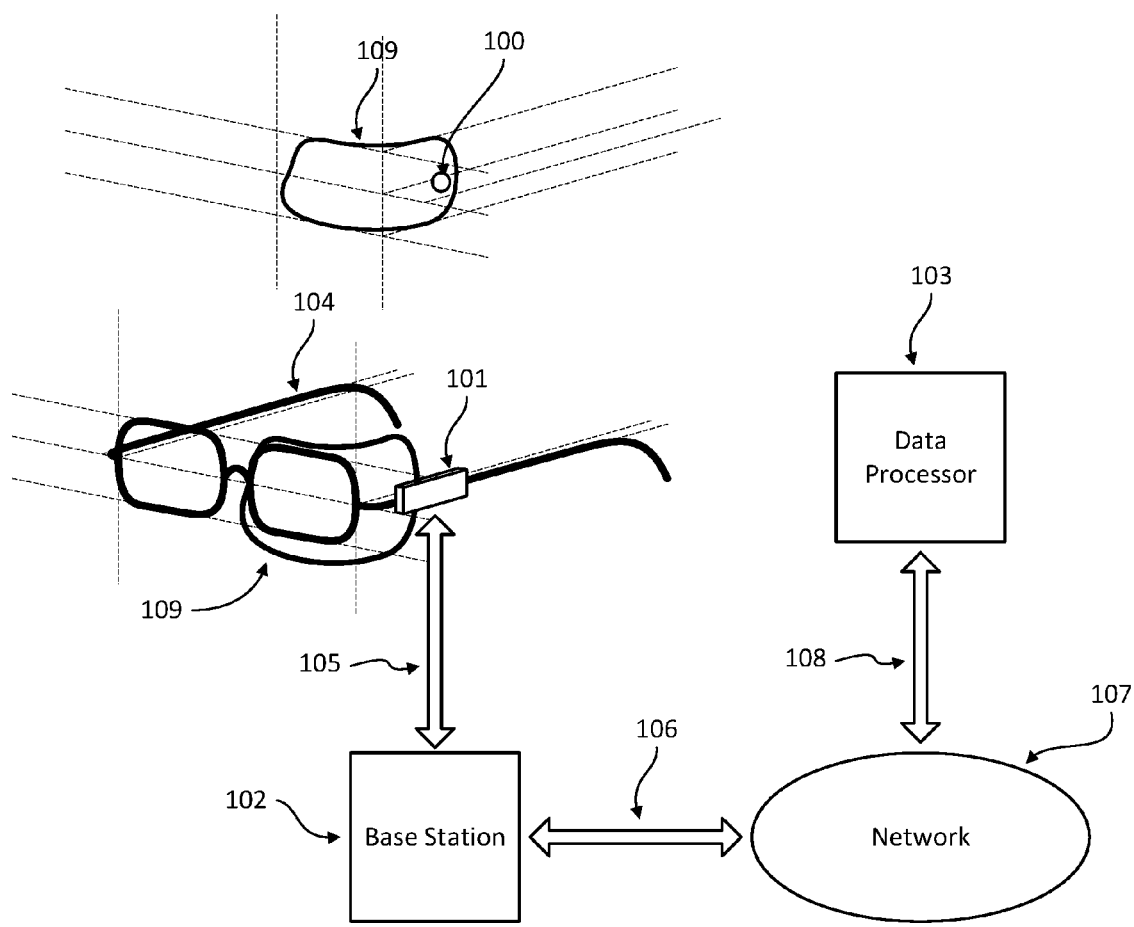
FIG. 1 is a block diagram of one embodiment of an occlusion dosage monitor (ODM).

Amblyopia is a vision disorder whereby information from one eye is not completely transmitted or not fully processed by the brain in favor of information from the other, "strong" eye. A common treatment modality for Amblyopia is the periodic occlusion of the "strong" eye for a prescribed duration over a specified time period. Occlusion may be achieved with an opaque "patch" that covers the eye or attaches to the eyeglass frame or lens. This method of periodic occlusion is commonly referred to as "patching". Patching is also used as a treatment of Strabismus and other vision disorders.

The system described in one embodiment utilizes a small magnet, in an eye patch such that the magnet is positioned on the side of the face in the region just behind the eye (or directly over the eye), or placed on or near where the lens and the leg of the spectacles meet (for the case of a patch on the lens), and one or more magnetometers to monitor compliance with the required wearing of the patch. This permits the use of a lightweight, simple, and cheap patch. It also permits adding a magnet to an existing patch.

The presence or absence of the magnet is monitored by a device in close proximity to the magnet. In one embodiment, the logging device may be attached to the adjacent leg ("temple") of a pair of eyeglasses. Alternatively, the logging device may be directly attached to the user, or to some other element of the user's daily wear or equipment in close proximity to the eye. The logging device makes and stores measurements of the magnetic field. Analysis of these measurements allows for a determination of those periods in time when the magnet is and is not present and further, when a magnet is present, it's disposition. In one embodiment, the distance from the nearest part of the device to the magnet may typically be less than three inches. In other applications this distance can be longer, or shorter.

The detection of the magnet takes account of the sharp spatial drop-off in the magnetic field from the magnet; the presence of the background magnetic field of the Earth with respect to which the temple and magnetometer(s) change orientation as the eyeglasses move with their wearer; and the measurement errors of practical magnetometers.

The goal is to provide, after a period of operation of a device, a time-series of numbers which when graphed allow identification of those time periods during which the magnet was present (patch on) and absent (patch off). In addition, the data may be used to determine when the eyeglasses were stationary and deduce when the glasses were not being worn. This is of value quite apart from knowing when the patch was on.

In one embodiment, one magnetometer may be used to detect a large enough magnet. In another embodiment, two magnetometers are used in combination to detect smaller/ weaker magnets. Because the magnet is worn, having a lower magnetic force, and smaller magnet is preferred, to minimize risks to health (swallowed magnets), electronic devices, and for comfort.

The below examples focus on an occlusion dosage monitor, but one of skill in the art would understand that the combination of magnet, magnetometer(s), and analysis described below may be applicable to other uses in which the disposition of an object may be monitored over time.

FIG. 1 illustrates one embodiment of the ODM system. The system in one embodiment includes a Modified Eye-Patch (109) with a magnet (100), a Logging Device (101), a Base Station or interrogator (102), and a Data Processor (103). The modified eye-patch (109) may be attached to the eyeglass lens, stuck over the user's eye, or attached in some other way to occlude the selected eye. The Logging Device (101) is kept in close proximity to the patch.

In one embodiment, the Logging Device (101) is mounted on a pair of eyeglasses (104) worn by the patient. Alternately, the Logging Device (101) may be attached to the user directly (taped-on or the like), or attached to some other wearable item associate with the user, such as head gear, which is worn by the user during waking hours.

The Logging Device (101) communicates with a Base Station (102) via a communication link (105). The communication link (105) may utilize, but is not limited to, a wired or wireless or optical connection. In one embodiment, the Logging Device (101) is designed to have enough memory to log data until the user visits the medical doctor, where the communication link (105) may be connected to the Logging Device (101), and the data may be downloaded. The communication link (105) may be a MicroUSB or other small form factor connector.

The Base Station (102) may connect to the Data Processor (103) for the purpose of data collation and analysis. To effect this connection, the Base Station (102) may have a connection (106) to the Internet (107). Similarly the Data Processor (103) may also have a connection (108) to the Internet (107). Alternatively the Base Station (102) and Data Processor (103) may communicate directly or via some other means. Alternatively, Base Station (102) may be within the same computing device as Data Processor (103) and they may communicate directly via an internal bus or similar communication mechanism.

Figure 2A:
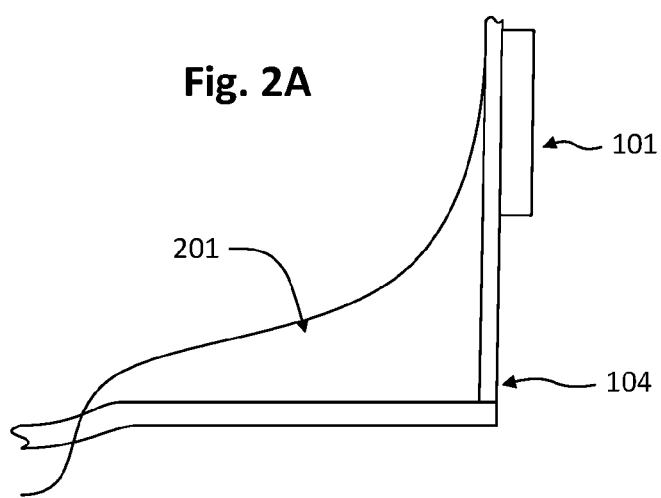
FIG. 2A illustrates one embodiment of a top view of the user's face, showing glasses and logging device.

The Logging Device (101) may be mounted on the eyeglasses (104) as depicted in FIG. 2A, in one embodiment. The curvature (201) represents the user's facial contour, depicted from above, with the glasses (104) and the attached logging device (101) also shown. In one embodiment, the Logging Device is positioned along the eyeglasses leg with a preference to position it as far from the eye as possible, while still maintaining detection range. In one embodiment, as shown, the Logging Device (101) may be mounted on the outside of the left arm of the Patient's eyeglasses to monitor the occlusion dose of the left eye. In the case when the right eye is to be patched the Logging Device (101) may be mounted on the outside of the right arm of the Patient's eyeglasses. Other mounting configurations may also be used. For example the logging device (101) may be mounted on the inside of the eyeglass frame. The particular mounting configuration may depend upon the size and style of the patient's eyeglasses.

Figure 3A:
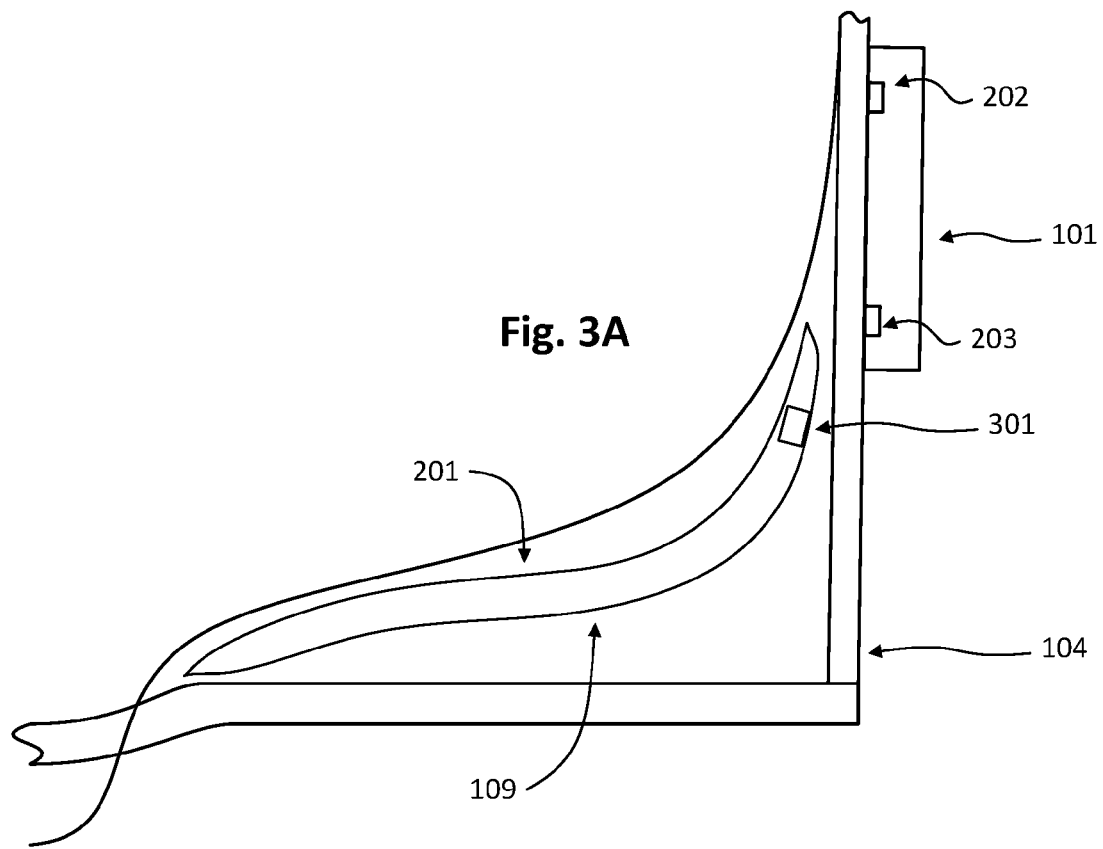
Figure 3B:
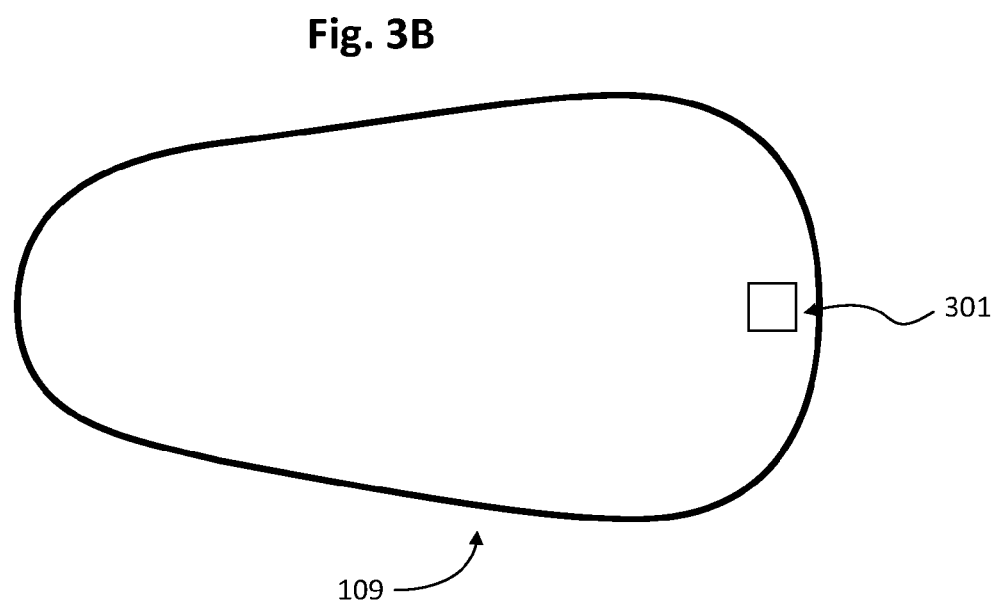
FIG. 3B illustrates an exemplary patch, showing one embodiment of a relative location of the magnet.

A modified eye patch (109) is shown in FIG. 3B. In one embodiment, it is of the type commonly used for amblyopia treatment. In one embodiment, the eye patch (109) is one of: an adhesive bandage patch which is applied to the user's face to cover the eye, a patch for attaching to the eyeglasses in front of or behind the lens, and an eye patch over the eye which is held in place by an elastic band or string. The patch (109) is customized by the addition of a magnet (301). The magnet (301) may be built into the eye patch, stuck on the eye patch, enclosed in a cover which is adhered to the outside of the eye patch, or inserted within the patch during manufacture. A magnet is considered to be any device that creates a magnetic field. In one embodiment, instead of a permanent magnet, magnet (301) may be multiple smaller magnets, an electromagnet, or something else which generates a magnetic field. The magnet is small in size and lightweight, to minimize discomfort to the wearer. In one embodiment, the magnets also have low magnetic field strength. This is for patient safety and for minimal interference with other devices or cards with magnetic stripe.

The magnet (301) in one embodiment is attached securely to, or embedded within, the patch (109) at a location on the outside edge of the patch. In one embodiment, the location of the magnet (301) is preferably in an area on or above the cheek. Generally patches are directional.

Figure 2B:
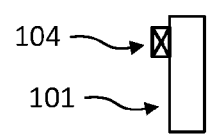
FIG. 2B illustrates a cross-section of the logging device and one glass arm, showing the relative positions.

FIG. 2B shows a cross section through the arm of the eyeglasses (104) and the Logging Device (101). The Logging Device is attached to the arm of the eyeglass by an attachment mechanism, such as heat shrink tubing, glue, epoxy, hook and loop fastener, screw, tension mount, clasp, etc. The logging device (101) should not move or shift with respect to the eyeglass leg. The attachment may be permanent or temporary. In one embodiment, the long axis of the Logging Device (101) is largely parallel with the eyeglasses leg (104), when attached. The same configuration may be used to monitor the left eye or the right eye. In one embodiment, rotation of the logging device (101) about this long axis, parallel with the eyeglass leg, allows mounting on the opposite eyeglass leg, enabling use of the same Logging Device (101) configuration, regardless of which site it is to be used for.

Figure 2C:
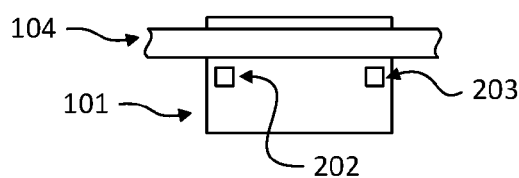
FIG. 2C illustrates an embodiment of the logging device showing two sensors.
Figure 2D:
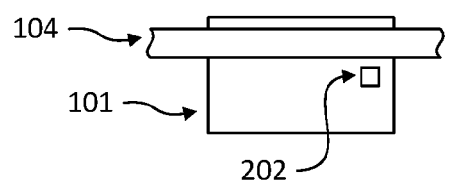
FIG. 2D illustrates one embodiment of the logging device showing one sensor.

The preferred embodiment contains two magnetic sensors (202 & 203) as shown in FIG. 2C. An alternate embodiment with a single sensor is shown in FIG. 2D. In one embodiment, as shown in FIG. 2C the two sensors are aligned along the long axis of the logging device, and placed relatively far from each other. The two magnetometers are further aligned with respect to each other such that the X axis of the first magnetometer is substantially parallel to the X axis of the other magnetometer, and similarly with the Y and Z axes. The sensors may also be placed in any orientation with respect to the eyeglasses. In one embodiment, the separation between the sensors is maximized within the constraints of the logging device enclosure. In one embodiment, the positioning of the two magnetometers is such that the magnetic field detected by each from the magnet in the patch is different due to the magnet's dipole field. This enables use of the spatially variable field to detect a smaller magnet more accurately, and will be discussed below.

The magnetic sensors (202, 203) each measure the intensity and direction of the magnetic field passing through them. That is, they measure the magnetic field vector passing through them.

In the real world, magnetometers although sensitive can provide wildly inaccurate readings, due to large offset and differing axis gains which can drift over time. However, analysis can circumvent these issues. Prior art magnetometer systems either ignore offsets and gains, and assume that measurements are highly accurate as well as sensitive, or require intense calibration methods prior to measurements being conducted.

The output measure of each of the magnetometer's axis measurements can be modeled as a linear function of the component of the magnetic field present in the direction of the axis in question, with an offset, and a smaller cross-coupling contribution from off-axis components of the magnetic field. We can approximate this mathematically, in vector form, as: $\underline{M} = \underline{A} + G \cdot \underline{B} + \underline{\epsilon}$ Where $\underline{M}$ is the measurement output 3-vector, with a component for each of the three axes.

$\underline{B}$ is the true 3-vector magnetic field being measured $\underline{A}$ provides the offset for each of the three axes.

G Is a mostly diagonal 3×3 matrix multiplying each of the components of $\underline{B}$ along a given axis, to contribute a measured effect along the same axis. The off-diagonal terms couple the components of $\underline{B}$ with measured effects in magnetometer axes orthogonal to them.

$\underline{\epsilon}$ is a 3-vector representation of the small random errors due to thermal fluctuations and transient interference effects within the electronic circuitry. It will have a zero mean.

Calibration of a non-ideal magnetometer can be attempted by rotating the magnetometer in a constant magnetic field and taking measurements at many orientations, and then running a mathematical algorithm to best fit the measurements to an ellipsoid. The result of this fit yields values for a constant $\underline{A}$ and G, and for the standard deviation of the random error, $\underline{\epsilon}$. Such calibration is not possible in the operation of a Logging Device and can be overcome through suitable analysis of the measurement output.

With a single magnetometer embodiment, in one embodiment, the process uses a shift in the range observed magnitude of $\underline{M}$ (|M|) values to discern those time periods when a magnet is present. With the dual magnetometers, in one embodiment, a shift in the |M| level is used to discern the presence of the magnet.

FIG. 5A shows modeled output of a single magnetometer with a relatively large magnet introduced and removed. The presence of the magnet can be clearly discerned by the jump in measured magnitude of the sensor's vector output. The period during which the magnet was present is designated by lines, beginning at time-point 93 and ending at time-point 231.

FIG. 5B shows the same single magnetometer and magnet disposition over time as in FIG. 5A but with a weaker magnet. It will be seen that the presence of the magnet cannot be reasonably discerned from the magnitude signal. This is because the magnet produces a field at the magnetometer which when added to the Earth's magnetic field cannot be distinguished from that of the Earth due to the inherent non-idealities of a practical magnetometer.

Figure 5C:
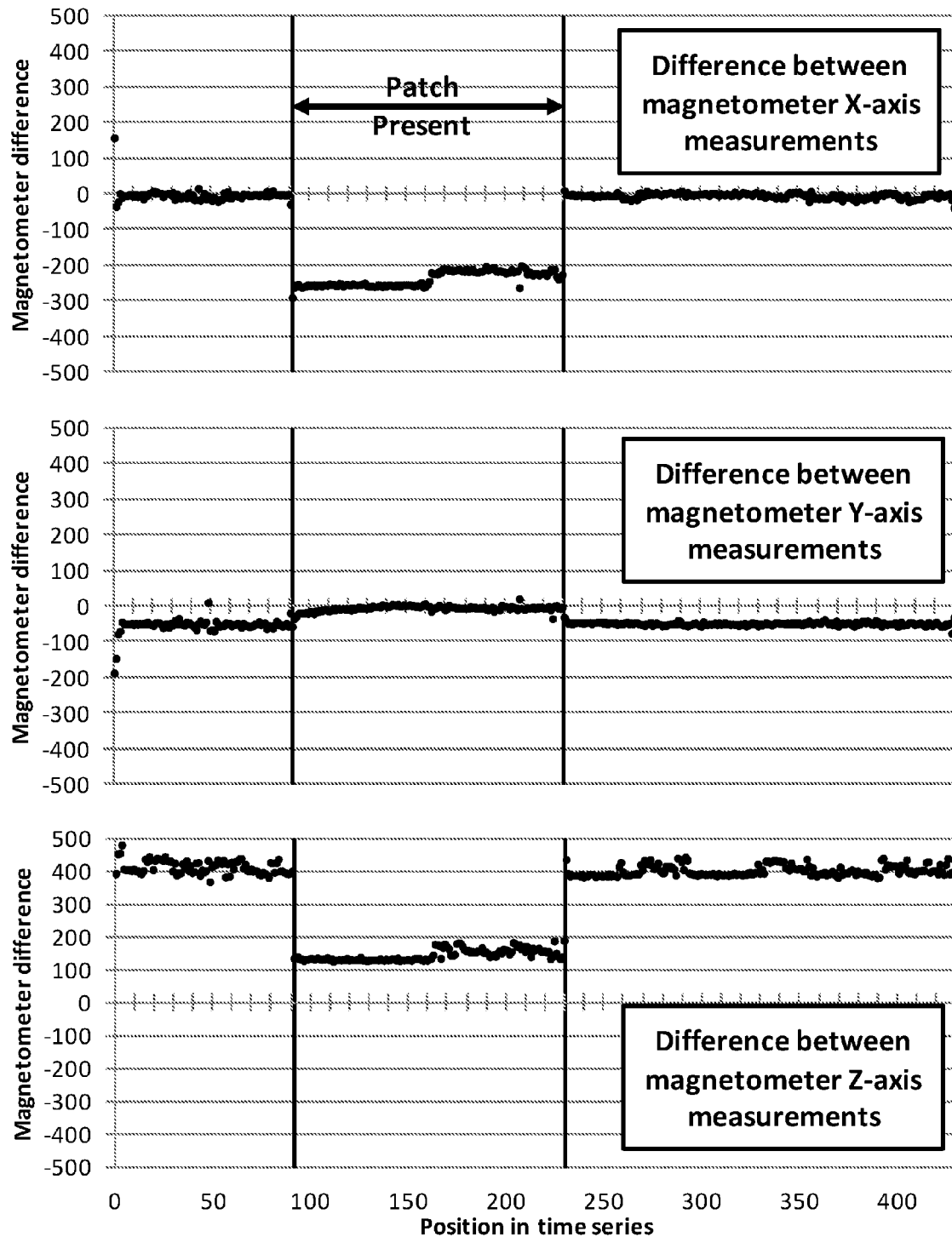
FIG. 5C illustrates an exemplary time-series output from an ODM with two magnetometers, and a small magnet.

FIG. 5C shows the results of an identical arrangement to that in FIG. 5B, but with the addition of a second magnetometer. FIG. 5C show the time plot of the difference in measured output of each magnetometer for each of the three aligned, orthogonal axes, X, Y and Z. The presence and absence of the magnet can now clearly be discerned.

These figures show that the operational regime of a single practical magnetometer will meet a limit at small magnet strength, and this limit can be surpassed by using a second magnetometer of same design, but using the difference vector.

FIG. 2D illustrates the alternative embodiment with a single magnetometer. The magnetometer may be positioned anywhere along the logging device. In one embodiment, the magnetometer is positioned along the portion of the logging device that is closest to the patch. In this embodiment the magnet must be sufficiently strong to make a contribution to the magnetic field at the single magnetometer sufficient to be detectable by the measurement process which combines the effects of offsets, different axis gains and the presence of the Earth's magnetic field. The small random errors, $\epsilon$ reduce the sensitivity but are small compared with typical offset and gain effects which greatly reduce the accuracy of M as a direct correlate of the magnetic field vector being measured. With this embodiment, the effects of other local fields such as telephones, headphones or other sources may be sufficient under certain circumstances to prevent a clear determination of the presence or absence of a magnet. The employment of operational rules adopted by the patient and care-giver limiting the presence of such magnetic field sources would allow full determination of the presence or absence of a magnet.

Figure 2E:
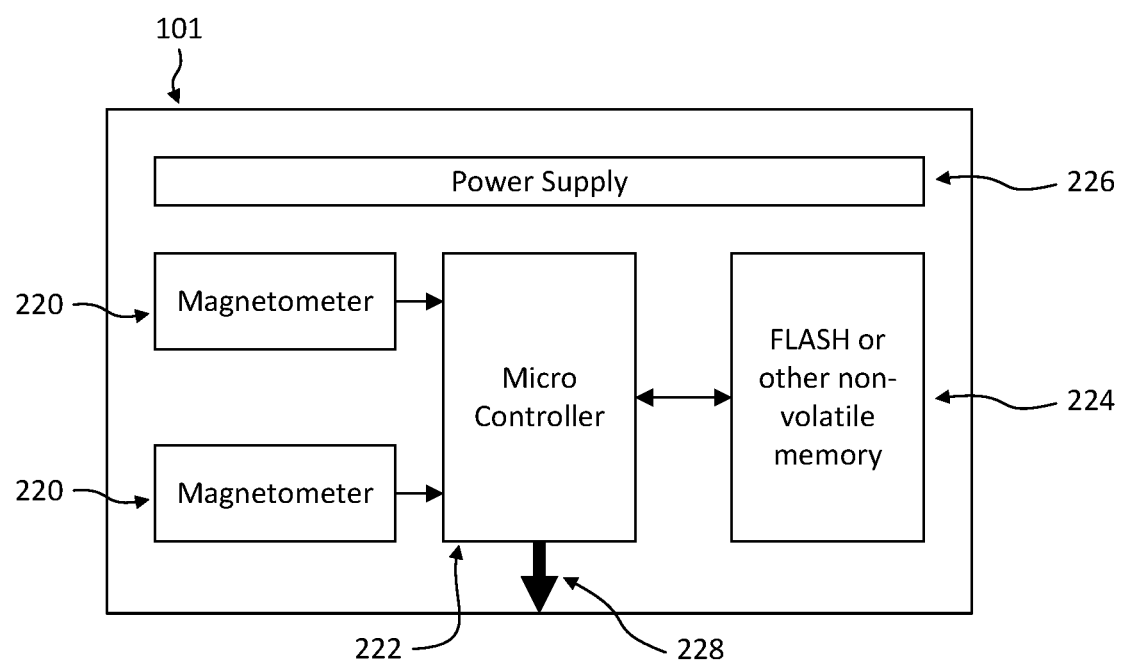
FIG. 2E is a block diagram of one embodiment of the logging device.

FIG. 2E shows one embodiment of the Logging device (101), which includes one or more magnetometers (220), a microcontroller (222), non-volatile memory (224) such as a Flash memory, a battery or electrical power source (226), and a connection mechanism (228). In one embodiment, the battery (226) may be a small watch battery. In one embodiment, the battery (226) may be rechargeable. In one embodiment, the microcontroller (222) is an Atmel ATtiny85. In one embodiment, the magnetometers (220) are 3-Axis Digital Compass IC HMC5883L by HONEYWELL™.

Figure 2F:
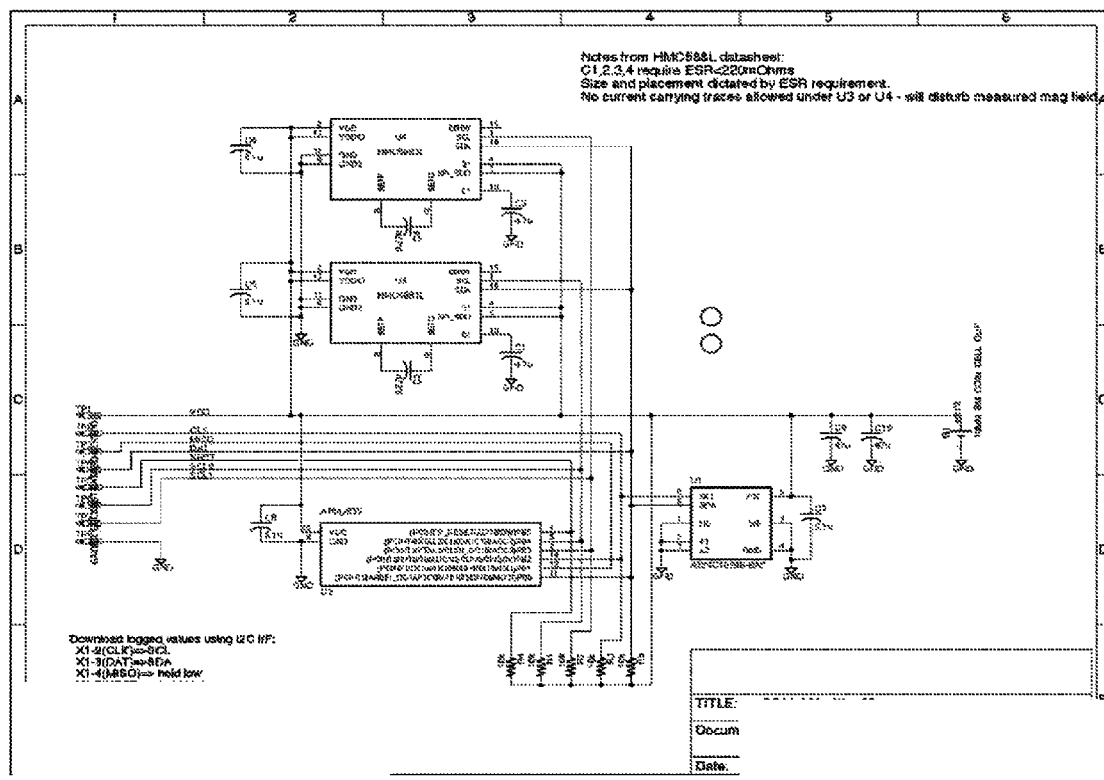
FIG. 2F is an exemplary circuit diagram of one embodiment of the logging device.

The connection mechanism (228) provides a method to communicate the data stored in the Logging Device (101) to the base station (102) described above. In one embodiment, the connection mechanism (228) also provides a path for communication from the Base Station (102) to the Logging Device (101). In one embodiment, the raw data received by the magnetometers (220) is processed by microcontroller (222) and stored in memory (224). In another embodiment, the raw magnetometer data is stored in memory, and processing is done in data processor (103) or other computer system remote from the logging device (101). Once stored, the data is available for download/access. FIG. 2F is an exemplary circuit diagram of one embodiment of the Logging Device.

One embodiment of the relative position of the magnet (301) and the magnetic sensors (202 & 203) is shown in FIG. 3A. The user's eye area/facial curvature 201 is partially covered by patch 109, which includes a small magnet 301. In one embodiment the patch adheres to the patient's face around the patch rim. The sensors (202 & 203) and magnet (301) need not be aligned. However in one embodiment the positioning of the logging device with respect to the magnet is optimized such that the magnetic field vector sensed by each magnetic sensor (202 & 203) is measurably different. This optimum position may depend on the shape and size of the patient's head and the configuration of the spectacles and patch.

When the magnet (301) is not present both magnetic sensors are subject to the Earth's magnetic field. The distance separating the magnetic sensors is small and so the Earth's magnetic field measured by the two sensors is assumed identical. When a strong dipole magnetic field, such as that generated by the magnet, is positioned relatively close to the logging device each magnetic sensor experiences a differing field vector. Since magnetic strength falls off at the cube of distance ($1/r^3$), even a small distance between the sensors will have a real impact on the magnetic field detected. In addition, if the magnet were equidistant from the two magnetometers, while the field strengths might be commensurate, their directions would differ. The foregoing may also be true for more complex fields, such as that from two or more magnets.

Therefore using a mathematical model of the dipole (or more complex) field, the relative position of the magnet with respect to the logging device may be inferred from the size and direction of the vector difference of the two sensors. Using this method, it is possible to infer if a patch is being worn or not. Other, local fields may be present temporarily, emanating from telephones, headphones, etc.—either while the eyeglasses are worn, stored or transported. Although such fields will also generate a vector difference in the magnetic fields of the two sensors, their size, orientation and variation in time will often be distinguishable from those of magnet on the patch when the Data Processor analyzes the measurements.

FIGS. 3C and 3D illustrate alternative patch configurations, in which the patch is attached to the eyeglasses either in front or behind the lens of the glasses, or is a freestanding or non-adhesive patch, secured with an elastic or similar attachment mechanism. The configuration of the patch is not limited, and merely requires a patch that can be modified with a magnet.

Figure 4:
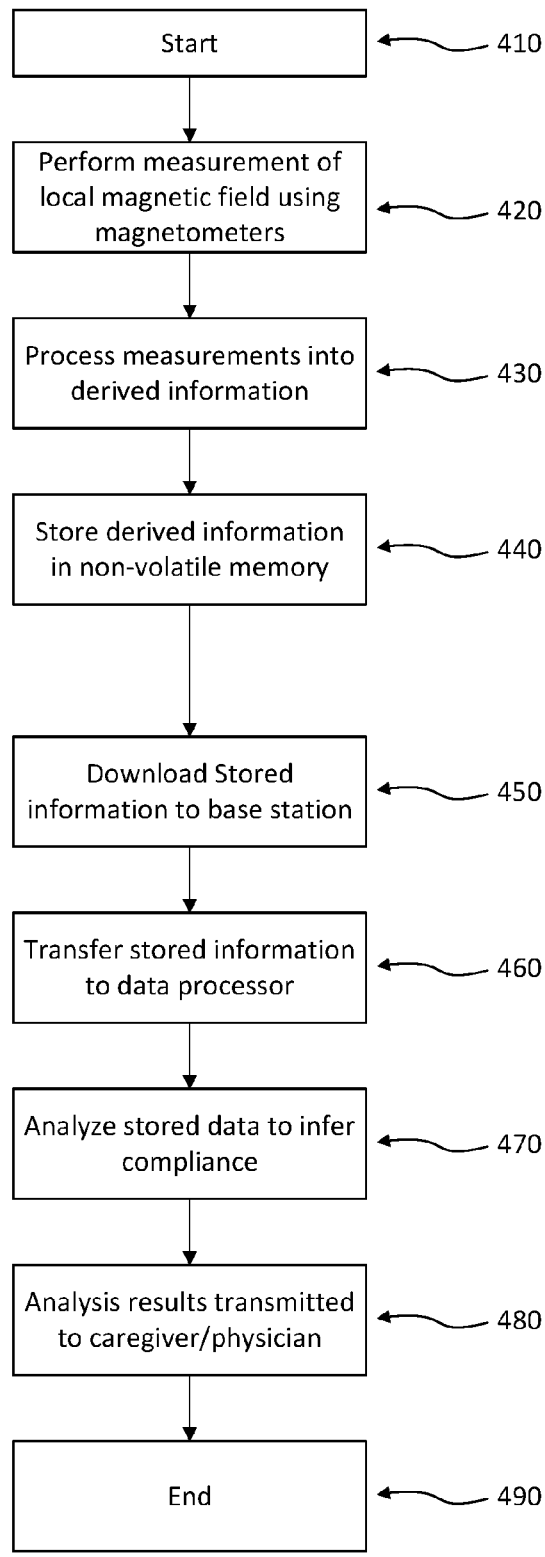
FIG. 4 is a flowchart of one embodiment of utilizing the system.

FIG. 4 is a flowchart of one embodiment of utilizing the system. The process starts at block 410, when the system is initialized.

At block 420, instructions are received from the Logging Device microcontroller to measure the magnetic field. In one embodiment, this is detected as a three-dimensional vector quantity from each magnetometer. In one embodiment, this occurs periodically. The period may be invariant, on the order of seconds, or minutes. The period may be variable depending on anticipated activity levels or time of day. In one embodiment the period is nominally invariant at one minute. In certain other embodiments the period may be controlled adaptively.

At block 430, these measurements may be examined by a program in the microcontroller to calculate derived information. In one embodiment, the derived information is a differential measurement between the two magnetometers to minimize the influence of earth's magnetic field. In other embodiments, this block is bypassed and the derived information may merely be the unchanged, raw measurements.

At block 440, the derived information is stored in memory. In one embodiment, the memory is non-volatile memory such as Flash memory. In one embodiment, the data is stored with time-stamp information. The derived information, together with the corresponding time-stamp information is collectively termed the "Data Log". In another embodiment, time stamp information is stored only on every N-th measurement, since the periodicity permits derivation of the actual time. In one embodiment, the time stamp information is stored only every 3 hours. In a further embodiment, no timestamp information is recorded, save for the time of the initiation of monitoring. The timestamps for each measurement are inferred by the position of the measurements in the data log, together with knowledge of the measurement period.

The data log, that is the time varying record of the two magnetic sensors measurements, may also be used to infer other useful data concerning the patient during the measurement period, in one embodiment. For example, variations in measured field over time indicate that the patient is awake, whereas a long period of non-movement indicates sleep. Periods during which the eyeglasses and sensors are being carried but not worn may be discernable by deducing their orientation with respect to the background magnetic field of the Earth. Knowing when the patient is wearing a patch whilst sleeping (which means the eyes are not being utilized) may be useful for the practitioner to make a more accurate assessment of the effective occlusion dosage.

At block 450, the data is communicated to a base station. The Logging Device includes a connection (105) which enables it to communicate with a Base Station. This connection may be used in both directions: for communication both to and from the Logging Device from and to the Base Station. One purpose of the connection is to download the Data Log stored in the Logging Device's memory to the Base Station. Another purpose of the connection may be to transfer diagnostic or other operating commands from the Base Station to the Logging Device. The connection (105) may be a wired connection such as USB/MicroUSB or wireless such as a Personal Area Network, for example a Bluetooth or NFC (Near-Field Communication) connection.

The Base Station (102) may be a personal computer, tablet, smart-phone, or customized device. The form of communication (105) between the Logging Device (101) and Base Station (102) may have different forms.

In addition, the Base Station has a connection to a Data Processor (103). This connection may be via the Internet (106, 107 & 108), a wired connection, an internal bus if the Base Station (102) resides on the same device as the Data Processor (103), or through an alternative mechanism.

In one embodiment, the Base Station (102) is used to regularly download the Data Log from the Logging Device (101). In one embodiment, the Base Station (102) may be at the office of a specialist treating the user. In another embodiment, the Base Station (102) may be the user's smart phone with an application enabling such a download. In one embodiment, a software program ("Client Software") on the Base Station is part of the preferred embodiment. The Client Software stores the downloaded Data Log on the Base Station's memory. In one embodiment, the connection may also be used to communicate status information, or updates, to the Logging Device.

At block 460, the data is provided to the Data Processor.

At block 470, the analysis of the captured Data is performed by the Data Processor (103). Analysis in one embodiment, processes the data and determines based on the data collected over a period of time, those sub-periods during which eyeglasses and a modified patch were worn together by the Patient. In one embodiment this analysis may be automated, in another it may be performed by a trained operator. In one embodiment, a second output of the analysis is a determination of those sub-periods during which the eyeglasses were worn but without a patch. In one embodiment, these determinations include a measure of confidence (a probable correctness of the determination.)

At block 480, the output of the analysis is provided to the Patient, his/her caregiver and to the physician. In one embodiment, the output may be provided via the Data Processor, the Base Station, another linked computer system or display system. In one embodiment, the output may be provided via email, text, application, or a website to authorized parties, including the patient. In one embodiment, the output is a chart of the times when the user was wearing the patch, and not wearing the patch. In one embodiment, a trained professional can then utilize this data to make recommendations, evaluate compliance, and potentially alert the patient's treatment plan based on the results.

In one embodiment, the system may alert the user, caregiver and/or physician's office of non-compliance. In one embodiment, an alert, may be sent. Some exemplary alerts may include: "To Doctor's office: Patient X has diverged from compliance please take a look." Or before that "To Caregiver: Patient is not patching the prescribed amount of time. Do you need any help?" Or potentially "To User: Please comply with the occlusion dosage prescribed."

The process then ends at block 490.

The magnetometer system may be used for other applications apart from occlusion monitoring. Exemplary applications include any application in which an object may include a magnet, and the object's disposition (positions and/or orientation) is relevant. The positions and/or orientation may be monitored with respect to rotational movements, translational movements, and combinations of rotational and translational movements. Examples of rotational movements include positions of a gate, door, lid, or any hinged object, where the monitoring may provide information about whether it is closed or ajar and to what degree. Other examples include a control dial or lever, actuator, spindle, wheel, faucet.

Examples of translational movements which can be monitored are sliding controls, doors, windows, drawers, lids & fluid levels. Furthermore, air movement may be detected by way of a small magnet suspended on a light fabric or vane. This method may determine whether a HVAC unit or a ceiling fan is active, for example. Alternatively it may be used to indicate the existence and direction of drafts within a room.

Applications combining rotational and translational motion may include monitoring of flexing members, eccentricity caused by bearing wear, weight scales, or a situation in which a deviation from any expected relative motion between objects occurs, such as an object which should be securely fastened during transportation. For example, flexure of a dog leash and therefore its use over a period of time can be monitored by attachment of a small magnet and the logging device to the leash.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

We claim:

1. A system comprising:
    a logging device including:
        a magnetometer designed to be in close proximity to a small magnet in an eye patch, the magnetometer to monitor a magnetic field, generated by the small magnet, earth, and proximate magnetic devices;
        a memory to store data from the magnetometer; and
        a communication link to obtain the data from the memory, the data processed to show a pattern of wearing and not-wearing the eye patch, to monitor compliance with a medical prescription.

2. The system of claim 1, wherein the logging device is attached to glasses.

3. The system of claim 1, further comprising:
    a second magnetometer designed to be in close proximity to the small magnet, a spatially varying field of the small magnet detected by the first and the second magnetometer.

4. The system of claim 1, further comprising:
    a microcontroller to control a timing of measurements of the magnetic field, and storing of the data.

5. The system of claim 1, further comprising:
    a base station to receive data from the logging device, the base station comprising one of: a smart phone, a computer application, and a special purpose device.

6. The system of claim 5, further comprising:
    a data processor to process the data from the logging device, the data processor to determine the pattern of wearing and not-wearing the eye patch, to monitor compliance with a medical prescription.

7. The system of claim 6, further comprising:
    a communication system to inform one or more of the user, a medical professional, and a designated party of the pattern.

8. The system of claim 1, further comprising:
    the eye patch comprising one of: an adhesive bandage patch which is applied to the user's face to cover the eye, a patch for attaching to the eyeglasses in front of or behind the lens, and an eye patch over the eye which is held in place by an elastic band or string.

9. An eye patch for improved monitoring of compliance with a medical protocol, the eye patch comprising:
    a covering portion to substantially cover one eye; and
    a magnet positioned on a side of the eye patch, such that when glasses are worn, a magnetometer positioned on the glasses can detect a magnetic field of the small magnet, the presence of the magnet used to determine the compliance with the medical protocol.

10. The eye patch of claim 9, wherein the magnet is one of: built into the eye patch, enclosed in a cover which is adhered to the outside of the eye patch, stuck on the eye patch, or inserted within the patch during manufacture.

11. The eye patch of claim 9, wherein the eye patch is one of: an adhesive bandage patch which is applied to the user's face to cover the eye, a patch for attaching to the eyeglasses in front of or behind the lens, and an eye patch over the eye which is held in place by an elastic band or string.

12. The eye patch of claim 9, wherein the medical protocol is for treatment of amblyopia.

13. A magnetometer-based monitoring system comprising:
    a magnet integrated with an object whose disposition is to be monitored, wherein the object is an eye patch worn by a user;
    a first magnetometer located in proximity to the object to detect a magnetic field of the magnet;
    a second magnetometer located at a fixed distance from the first magnetometer in proximity to the object to detect the magnetic field of the magnet;
    a processor to receive data from the first magnetometer and the second magnetometer, and calculate a measurement difference 3-vector to determine the disposition of the object based on data from the first magnetometer and the second magnetometer and unknown rotations of the object in Earth's magnetic field.

14. The magnetometer-based monitoring system of claim 13, wherein the first magnetometer and the second magnetometer are in a logging device.

15. The magnetometer-based monitoring system of claim 14, wherein the logging device further comprises a microprocessor and a memory.

16. The magnetometer-based monitoring system of claim 13, wherein the disposition of the object determines whether a user is wearing an eye patch including the magnet, to monitor compliance with a medical protocol.

17. The magnetometer-based monitoring system of claim 16, wherein the protocol is treatment of amblyopia.

18. The magnetometer-based monitoring system of claim 13, further comprising:

a memory to store data from the first magnetometer and the second magnetometer; and a communication link to communicate data from the memory to the processor.

19. The magnetometer-based monitoring system of claim 18, further comprising:

a microprocessor to obtain the data from the first magnetometer and the second magnetometer, and store the data in the memory.

* * * * *